United States Patent [19]

Chai et al.

[11] 4,239,695

[45] Dec. 16, 1980

[54] METHOD OF PREPARING PHOSPHONATES FROM NITRILES

[75] Inventors: Bong J. Chai, West Covina; Fred D. Muggee, Anaheim, both of Calif.

[73] Assignee: Magna Corporation, Santa Fe Springs, Calif.

[21] Appl. No.: 780,883

[22] Filed: Mar. 24, 1977

[51] Int. Cl.$^3$ .................... C07F 9/38; C07C 121/16; C07D 213/53
[52] U.S. Cl. ................................ 260/502.5; 210/700; 260/465.5 R; 546/22
[58] Field of Search .................... 260/502.5, 465.5 R; 546/22

[56] References Cited

U.S. PATENT DOCUMENTS

| 3,565,949 | 2/1971 | Cummins | 260/502.5 |
| 3,919,296 | 11/1975 | Schindler et al. | 260/502.5 |

FOREIGN PATENT DOCUMENTS

| 1002355 | 2/1957 | Fed. Rep. of Germany | 260/502.5 |
| 995462 | 6/1965 | United Kingdom | 260/502.5 |

*Primary Examiner*—Joseph E. Evans
*Attorney, Agent, or Firm*—Knobbe, Martens, Olson, Hubbard & Bear

[57] ABSTRACT

Amino-phosphonates typified by the general formula R—C(PO(OH)$_2$)$_2$NH$_2$ are prepared by reacting phosphorous acid with nitriles at elevated temperatures.

11 Claims, No Drawings

METHOD OF PREPARING PHOSPHONATES FROM NITRILES

This invention relates to a novel process for preparing organo-alphaamino-diphosphonic acids having the general structural formula

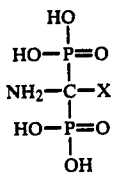

wherein X may be:

II R,

R being a saturated or unsaturated aliphatic radical having from 1 to about 22 carbon atoms or phenyl, benzyl or naphthyl radical or substituted aliphatic or aromatic radicals;

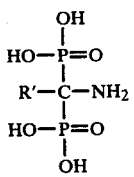

R' being an aliphatic bridging radical having from 1 to about 10 carbon atoms;

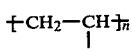

where n is a positive integer of 2 or greater; and
—R'—C≡N

R' being the same as defined above. More specifically, this invention relates to the preparation of compounds of the class defined by the reaction of phosphorous acid and an organic nitrile.

The aminophosphonates characterized by formula I having substituents II, III and IV are known and have established utility as wetting agents. These aminophosphonates exhibit detergency and a range of solubility from high solubility in water to high solubility in oil, depending upon the size of the hydrocarbon moiety of the molecule. These compounds are useful as water softening agents for boilers, in water cooling towers and as scale inhibitors for conate waters associated with crude oil production. These compounds are also useful for treatment of injection waters for secondary or tertiary oil recovery and have application as corrosion inhibitors in corrosive fluids containing dissolved gases such as oxygen, carbon dioxide and hydrogen sulfide. These amino-phosphonates have application as thinning agents for aqueous slurries of inorganic materials such as clays, talc, and whiting. In general, these aminophosphonates are surface active agents which exhibit chelating properties.

Compounds having the generic formula I which the substituents II and III have been prepared by the reaction of phosphorous trihalides, with nitriles and, subsequently, with water, see German Pat. No. 1,002,355, Feb. 14, 1957; U.S. Pat. No. 3,303,139, Feb. 7, 1967; British Pat. Nos. 1,243,347, Aug. 18, 1971 and 1,381,668, Jan. 22, 1975. These references, variously, discuss the synthesis of compounds of the generic class I with substituents II and III, salts thereof, and the utility of these compounds and derivatives and salts thereof as sequestering and complexing agents as well as builders in detergent compositions.

These amino-phosphonates are also obtained by reacting phosphorous acid with carboxylic acid amides at elevated temperatures with the introduction of hydrogen chloride gas, treating the reaction mixture with steam, see German Pat. Nos. 2,048,912, Apr. 13, 1972, 2,115,737, Oct. 12, 1972, and 2,203,340, Aug. 2, 1973. Various useful applications of these compounds are disclosed in these patents also.

The known processes suffer from serious technical and practical disadvantages. For example, in the reaction of phosphorous trihalides with nitriles, satisfactory yields are obtained only when using the very expensive and corrosive reactant phosphorous tribromide. Similarly, the reaction of phosphorous acid with carboxylic acid amides and hydrogen chloride must be carried out in special corrosion resistant equipment because of the highly corrosive characteristics of hydrogen chloride at elevated temperatures.

One of the features of this invention is that these disadvantages have been overcome in that it is possible to produce, in a simple and efficient process, compounds having the generic formula I. One of the characteristics of this new process is that, without the presence of hydrogen chloride or hydrogen bromide, phosphorous acid is reacted with organic nitriles at elevated temperatures.

Typical examples of organic nitriles are acetonitrile, propionitrile, acrylonitrile, allylcyanide, amylnitrile, anisylcyanide, benzonitrile, benzylcyanide, chloroacetonitrile, aminoethylnitrile, crotonitrile, cyanoacetamide, 2-cyanoethyl acrylate, 2-cyanopyridine, 3-cyanopyridine, b-ethoxyacrylonitrile, ethoxymethylene malonitrile b-hydroxypropionitrile, lactonitrile, isobutyronitrile, malononitrile, methylcyanoacetate, 4-cyanopyridine-N-oxide, 3, 3'-thiodipropionitrile, o-toluonitrile, polyacrylonitrile, adiponitrile, nitrilotriacetonitrile, tallownitrile, and, in general, organonitrile compounds. HCN and cyanogen are obvious reagents for use in this process and are under evaluation.

The process according to this invention is carried out at elevated temperatures, generally in the range of from about 100° C. to about 200° C. The preferred range for carrying out the reaction is from about 135° C. to about 160° C. Since the reaction is exothermic, it is advantageous to keep one reactant at near the desired elevated temperature and to introduce the other reactant slowly into the reactor. When using lower boiling organic nitriles, it is necessary to introduce the organic nitriles with the lower boiling points into the phosphorous acid within the desired temperature range to achieve a practical rate of reaction. The reaction period depends upon the rate of reaction of the particular organic nitrile being introduced into the reactor but the reaction is generally complete within from about two hours to about fifteen hours.

Amino-phosphonic acids can be prepared according to the principles of this invention without the use of a solvent; however, in most instances the reaction mixtures become a solid or viscous mass in the absence of a solvent. Processing is simplified if a solvent is used.

Phosphorous acid is a convenient solvent since it serves not only as the reactant but excess phosphorous acid serves well as a solvent. Other solvents include, generally, organic acid, e.g., acetic acid, propionic acid, etc., dimethylsulfoxide, sulfolane, chlorinated aromatic solvents and other highly polar non-aqueous solvent materials.

Once formed, amino-phosphonic acids prepared according to this invention, may be precipitated by simply adding a suitable quantity of water or organic solvent, e.g., acetone or lower alcohol, to the reaction mixture to be worked up. The amino-phosphonic acids are only slightly soluble in these solvents and precipitate out readily.

Within the general principles of the invention as previously discussed, there is considerable latitude for variation to optimize reaction rate and yield. The following examples are given to illustrate various conditions under which the reaction of this invention can be carried out. These examples are not limiting and are not intended to define the outer parameters of the useful ranges of the process variables.

EXAMPLE 1

Into a 250 ml three-necked round bottomed flask, suspended in an oil bath, equipped with a three way adapter, carrying a pressure equalizing addition funnel, a reflux condenser attached to a calcium sulphate tube, a mechanical stirrer and a thermometer was placed 260 g phosphorous acid. 33 g acetonitrile was introduced slowly over a 2 hour period into the agitated phosphorus acid held at a temperature of 138°–142° C. The mixture was held for an additional 12 hours at that temperature after completing addition of the nitrile. The 1-aminoethane-1, 1-diphosphonic acid produced was precipitated with methanol.

The yield was 85% of the theory calculated on the acetonitrile employed. By NMR (both $P^{31}$ and $H^1$) spectra the precipitate was wholly 1-aminomethane-1, 1-diphosphonic acid.

|  | C | H | N | P |
|---|---|---|---|---|
| Calculated | 11.71% | 4.42% | 6.83% | 30.21% |
| Found | 11.83% | 4.43% | 6.92% | 30.18% |

EXAMPLE 2

Into a reactor similar to the above were charged 174 g phosphorous acid and 92 g propionic acid. 41.5 g acetonitrile was introduced slowly for 72 minutes at 135°–140° C. into the agitated mixture which was maintained for an additional 10 hours at that temperature. The 1-aminoethane-1, 1-diphosphonic acid produced was isolated from the reaction mixture in the same manner as described in Example 1. The yield was 85% of the theory calculated on the acetonitrile employed.

EXAMPLE 3

Into a reactor like the above were charged 130.5 g phosphorous acid and 69 g Sulfolane-W (tetramethylene sulfone, Shell Chemical Co.). 31.2 g acetonitrile was introduced slowly for 1½ hours at 140°–150° C. and the reactants were held for additional 8½ hours at 153°–158° C. The 1-aminoethane-1, 1-diphosphonic acid produced was isolated from the reaction mixture in the manner described in Example 1. The yield was 75% of the theory on the acetonitrile employed.

EXAMPLE 4

Into a reactor like the above was charged 261 g phosphorous acid. 44.3 g propionitrile was introduced slowly for 70 minutes at 135°–143° C. into the agitated phosphorous acid. The reactant mixture was held for additional 10 hours at 150°–155° C. The 1-aminopropane-1, 1-diphosphonic acid produced was isolated from the reaction mixture in the manner described in Example 1.

The yield was 71% of the theory calculated on the propionitrile employed.

EXAMPLE 5

Into a reactor like the above was charged 97.9 g phosphorous acid. 31.3 g benzonitrile was introduced slowly for 1½ hours at 153°–158° C. into the agitated phosphorous acid and the reactant was held for additional 8½ hours at this temperature. The product was isolated from the reaction mixture in the manner as in Example 1. The yield was 37% of the theory calculated on the benzonitrile employed.

EXAMPLE 6

Into a reactor like the above was charged 164 g phosphorous acid. 27.3 g 1, 4-dicyanobutane was introduced slowly for 2½ hours at 153°–158° C. into the agitated phosphorous acid. The mixture was held for additional 11½ hours at that temperature. The product was isolated from the reaction mixture in the manner of Example 1. The yield was 49% of the theory calculated on the 1,4-dicyanobutane employed.

EXAMPLE 7

Into a reactor like the above, except that the pressure equalizing addition funnel was replaced with a dropping funnel, was charged 65.25 g phosphorous acid. 20.75 g 4-cyanopyridine was introduced portionwise during 70 minutes while maintaining a temperature of 135°–138° C. in the flask. The reactants were held for an additional 12 hours at that temperature. The product was isolated from the reaction mixture in the same manner as Example 1. The yield was 86% of the theory calculated on the 4-cyanopyridine employed.

EXAMPLE 8

Into a reactor similar to that of Example 1 was charged 82 g phosphorous acid. 50 g tallownitrile (Arneel T. Armak) was introduced slowly into the acid over a 2 hour period stirring and maintaining flask contents at 150°–160° C. The mixture was kept for additional 8 hours at that temperature. The product produced was precipitated with isopropyl alcohol. The yield was 53% of the theory calculated on the Arneel T employed.

Certain aminophosphonates were found to inhibit precipitation of $CaCO_3$ from solutions. A $CaCO_3$ precipitation test was performed as follows:

Synthetic brines:

| Brine A: | 12.15 gm/l $CaCl_2 \cdot 2H_2O$ | (reagent grade) |
|---|---|---|
|  | 3.68 gm/l $MgCl_2 \cdot 6H_2O$ | (reagent grade) |
| Brine B: | 7.36 gm/l $NaHCO_3$ | (reagent grade) |
|  | 0.0294 gm/l $Na_2SO_4$ | (reagent grade) |
|  | 66.0 gm/l NaCl | (reagent grade) |

Brines A and B were saturated with $CO_2$ immediately before using. 50 ml of Brine A was added to each test cell and mixed with inhibitor, then 50 ml of Brine B was added and mixed. Cells were capped tightly to avoid loss of $CO_2$ (Duplicates were run of each concentration). Two controls (blanks) were set up with each test. Test cells were placed in water bath at 160° F. (71° C.) for 24 hours, then filtered and the amount of calcium ion in the filtrates was determined by atomic absorption spectroscopy. The results of these tests are summarized in Table 1.

TABLE 1

Inhibition of $CaCO_3$ Precipitation
[Y in the structures below represents - P(O) (OH)$_2$]

| Compound | Concentration, ppm of Compound | Precipitation Inhibition, percent |
|---|---|---|
| $CH_3C(Y)_2NH_2$ | 2.5 | 81 |
|  | 5.0 | 84 |
| Potassium salt of $CH_3C(Y)_2NH_2$ | *5.0 | 84 |
| $H_2N(Y)_2C(CH_2)_4C(Y)_2NH_2$ | 2.5 | 42 |
|  | 5.0 | 57 |
| ⟨O⟩—C(Y)$_2$NH$_2$ | 2.5 | 9 |
|  | 5.0 | 31 |

*concentration based on acid.

Another screening test for $CaCO_3$ scale inhibition was performed as follows. Stock solutions (Deionized water is used):

$Na_2CO_3$ stock solution: 0.212 gm/l $Na_2CO_3$ $CaCl_2$ stock solution: 0.294 gm/l $CaCl_2.2H_2O$ 100 ml of $Na_2CO_3$ stock solution was added to each test cell with inhibitor and mixed. Then 100 ml of $CaCl_2$ stock solution was added to each test cell to form 100 mg/l $CaCO_3$ solution. A control (blank) was set up. The pH of the solution was adjusted to 10.3. The tightly capped cells were placed in water bath at 150° F. for 24 hours. 10 ml of $CaCl_2$ stock solution was transferred into 30 ml of deionized water in a beaker containing two drops of 50% caustic (pH>10) and titrated with EDTA solution (1 ml=0.10 mgms $CaCO_3$) using hydroxy naphthol blue indicator. One half the calcium content of the stock solution was taken as the initial calcium ion content of all test cells. In a similar manner filtrates from the test cells were titrated and EDTA solution required was recorded.

In mg per liter $CA^{++}$:

A = Initial $CA^{++}$ content of all solutions
B = Final $Ca^{++}$ content of test solution
C = Final $Ca^{++}$ content of blank solution percent C = Final $CA^{++}$ content of blank solution percent $$\text{inhibition} = \frac{B - C}{A - C} \times 100$$

The results of this test are shown in Table II

TABLE II

| Inhibitor Compound | $Ca^{++}$, initial mg/l | $Ca^{++}$, mg/l | Titrant .001 MEDTA Vi | Vf | ml | $Ca^{++}$, Final | Percent Inhibition | Notes |
|---|---|---|---|---|---|---|---|---|
| Blank | 0 | 40 | 2.30 | 6.80 | 4.50 | 18.0 | 0 | PH10.3 |
| 1-aminoethane | | | | | | | | |

TABLE II-continued

| Inhibitor Compound | $Ca^{++}$, initial mg/l | $Ca^{++}$, mg/l | Titrant .001 MEDTA Vi | Vf | ml | $Ca^{++}$, Final | Percent Inhibition | Notes |
|---|---|---|---|---|---|---|---|---|
| 1,1-diphosphonic Acid | .20 | 40 | 0.00 | 10.30 | 10.3 | 41.2 | 100 | PH10.3 |
|  | .30 |  | 10.30 | 20.70 | 10.4 | 41.6 | 100 |  |
|  | .40 |  | 20.70 | 31.40 | 10.7 | 42.8 | 100 |  |
|  | .50 |  | 31.40 | 42.10 | 10.7 | 42.8 | 100 |  |

A new process and specific exemplary processes have been disclosed for producing aminophosphonic acids having the formula shown below.

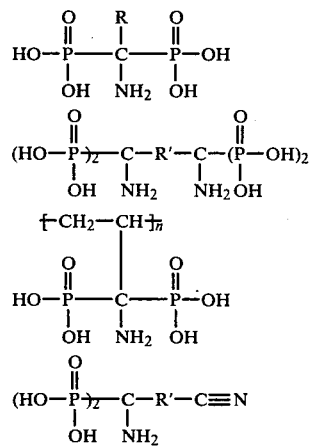

In these formulae, R. is a saturated or unsaturated aliphatic radical having 1–22 carbon atoms or phenyl or benzyl or naphthyl radical or substituted aliphatic or aromatic radicals. R' is difunctional aliphatic bridging radical having 1–10 carbon atoms. n is $\geq 2$. Generally, the first three products are preferred. The foregoing description and examples disclose the invention, but the scope of the invention is defined in the following claims.

We claim:

1. The process for producing aminophosphonic acids having the following formulae,

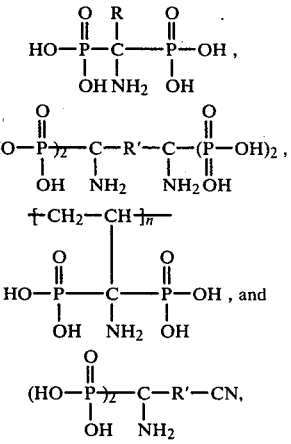

wherein R is a saturated or unsaturated aliphatic radical having 1-22 carbon atoms or phenyl or benzyl or naphthyl radical or substituted aliphatic or aromatic radicals, R' is a difunctional aliphatic bridging radical having 1-10 carbon atoms, and n is $\geq 2$, comprising reacting at a temperature of from about 100° C. to about 200° C. a mixture consisting essentially of phosphorous acid and an organonitrile selected from the group consisting essentially of R—CN, NC—R'—CN and

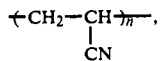

R being a saturated or unsaturated aliphatic radical, or phenyl, benzyl or naphthyl or substituted aliphatic or aromatic radical, R' being an aliphatic bridging radical, and n being a positive integer of 2 or greater.

2. The process for producing aminophosphonic acids having the formula

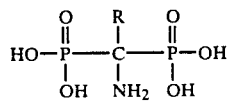

wherein R is a saturated or unsaturated aliphatic radical having 1-22 carbon atoms or phenyl or benzyl or naphthyl radical or substituted aliphatic or aromatic radicals, comprising reacting a mixture at temperatures of from about 100° C. to about 200° C., said mixture consisting essentially of phosphorous acid and an organonitrile of the formula R—C≡N wherein R is a saturated or unsaturated aliphatic radical having 1-22 carbon atoms or phenyl or benzyl or naththyl radical or substituted aliphatic or aromatic radicals.

3. The process for producing aminophosphonic acids having the formula

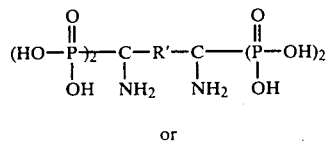

or

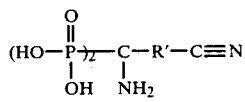

wherein R' is a aliphatic bridging radical having 1-10 carbon atoms, comprising reacting a mixture at a temperature of from about 100° C. to about 200° C., said mixture consisting essentially of phosphorous acid with an organo-dinitrile of the formula N≡C—R'—C≡N wherein R' is an aliphatic bridging radical having 1-10 carbon atoms.

4. The process for producing aminophosphonic acids having the formula

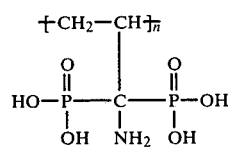

wherein n is a positive integer equal to or greater than 2 comprising reacting a mixture at a temperature of from about 100° C. to about 200° C., said mixture consisting essentially of phosphorous acid with an organonitrile of the formula

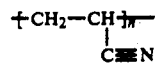

wherein n is a positive integer equal to or greater than 2.

5. The process for preparing organo-alphaaminodiphosphonic acids having the general structural formula

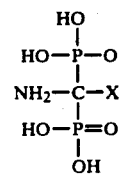

where X is:
R, R being a saturated or unsaturated aliphatic radical having from 1 to about 22 carbon atoms or phenyl, benzyl or naphthyl radical or substituted aliphatic or aromatic radicals; or

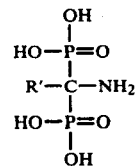

R' being an aliphatic bridging radical having from 1 to about 10 carbonatoms; or

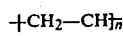

where n is a positive integer of 2 or greater; or

R' being an aliphatic bridging radical having from about 1 to about 10 carbon atoms, comprising reacting at a temperature of from about 100° C. to 200° C. a mixture, said mixture consisting essentially phosphorous acid with an organonitrile selected from the group consisting of R—CN, NC—R'—CN and

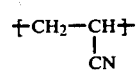

R being a saturated or unsaturated aliphatic radical having from about 1 to about 22 carbon atoms or phenyl, benzyl or naphthyl radical or substituted aliphatic or aromatic radicals, R' being an aliphatic bridging radical having from 1 to about 10 carbon atoms, and n being a positive integer of 2 or greater.

6. The process of claim 5 wherein the reaction is carried out at a temperature of at least about 100° C.

7. The process of claim 5 wherein the reaction is carried out at a temperature of from about 135° C. to about 160° C.

8. The process of claim 5 wherein the reaction is carried out in a solvent.

9. The process of claim 8 wherein the reaction is carried out at a temperature of from about 135° C. to about 160° C.

10. The process of claim 9 wherein the solvent is excess phosphorous acid, an organic acid, dimethylsulfoxide, tetramethylene sulfone, or chlorinated aromatic hydrocarbon.

11. The process for producing 1-aminoalkane-1,1-diphosphonic acid of the formula

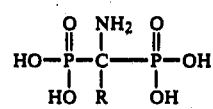

wherein R is an alkyl radical, which comprises reacting at a temperature between about 140° C. and about 200° C., a mixture consisting essentially of phosphorous acid and a nitrile of the formula R—CN, R being defined as above.

* * * * *